United States Patent [19]

Narandja et al.

[11] Patent Number: 5,023,240
[45] Date of Patent: Jun. 11, 1991

[54] DERIVATIVES OF TYLOSIN AND 10,11,12,13-TETRAHYDRO TYLOSIN AND THEIR USE IN PHARMACEUTICALS

[75] Inventors: Amalija Narandja; Bozidar Suskovic; Slobodan Djokic; Nevenka Lopotar, all of Zagreb, Yugoslavia

[73] Assignee: Sour Pliva, Yugoslavia

[21] Appl. No.: 180,940

[22] Filed: Apr. 13, 1988

[30] Foreign Application Priority Data

Apr. 14, 1987 [YU] Yugoslavia .................... 674/87

[51] Int. Cl.$^5$ .................. A61K 31/70; C07H 17/08
[52] U.S. Cl. ........................... 514/30; 536/7.1
[58] Field of Search ................ 514/30; 536/7.1

[56] References Cited

U.S. PATENT DOCUMENTS

| | | | |
|---|---|---|---|
| 3,910,892 | 10/1975 | Chonekar et al. | 549/378 |
| 4,205,163 | 5/1980 | Mori et al. | 536/7.1 |
| 4,594,338 | 6/1986 | Omura et al. | 536/7.1 |
| 4,680,386 | 7/1987 | Morimoto et al. | 536/7.2 |

FOREIGN PATENT DOCUMENTS

| | | | |
|---|---|---|---|
| 0785191 | 10/1957 | European Pat. Off. | 536/7.1 |
| 0070170 | 1/1983 | European Pat. Off. | 536/7.1 |
| 2221695 | 9/1987 | Japan | 536/7.1 |

*Primary Examiner*—Elli Peselev
*Attorney, Agent, or Firm*—Pollock, Vande Sande & Priddy

[57] ABSTRACT

Derivatives of tylosin and 10,11,12,13-tetrahydro tylosin of the general formula

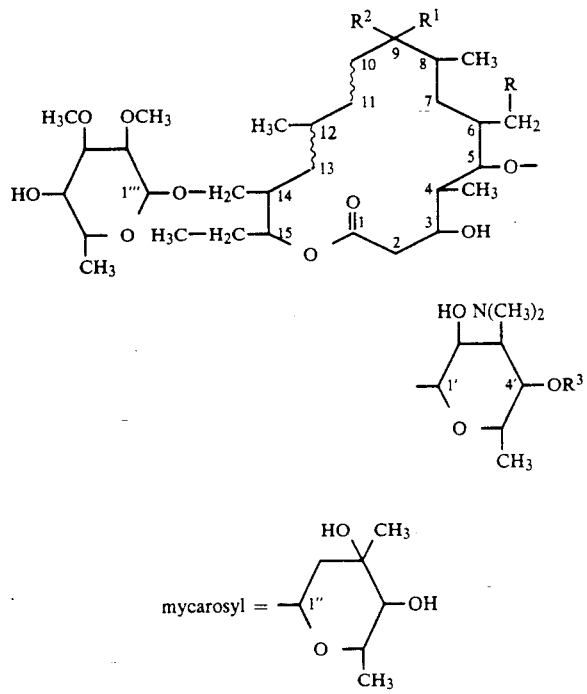

wherein
R stands for CHO, CH$_2$OH, CH=NOH or CH(OCH$_3$)$_2$,
R$^1$ stands for H,
R$^2$ stands for OH or
R$^1$+R$^2$ stand for =O or =NOH,
R$^3$ stands for a mycarosyl group or a hydrogen atom, and
 stands for a single or a double bond;

methods for the manufacture thereof; their use as antimicrobial agents and processes for the preparation of the latter.

24 Claims, No Drawings

DERIVATIVES OF TYLOSIN AND 10,11,12,13-TETRAHYDRO TYLOSIN AND THEIR USE IN PHARMACEUTICALS

The present invention relates to novel biologically active compounds of the tylosin series, specifically to tylosin oximes, to 10,11,12,13-tetrahydro tylosin, to derivatives of 10,11,12,13-tetrahydro tylosin and to oximes of 10,11,12, 13-tetrahdro tylosin and of its derivatives, to methods for the manufacture thereof, and to their use in the manufacture of pharmaceuticals, especially antimicrobial agents.

Tylosin (I) is a 16-membered macrolide antibiotic, used in veterinary practice. It is characterized by two neutral sugars, one basic sugar and, in the aglicone moiety of the molecule, by a conjugated double bond in the C-10,11,12,13 position, an aldehyde in C-20 position and a ketone in C-9 position. It is known that several tylosin derivatives have been prepared and it should be noted for a better understanding of the present invention that there are known the following dyhydro and tetrahydro derivatives of tylosin: 9-deoxo-9-hydroxy tylosin (Ie) (Tetrahedron Lett. 1977 (12) 1045), 20-deoxo-20-hydroxy tylosin (Ia) (tylosin D, relomycin) and 9,20-dideoxo-9,20-dihydroxy tylosin (J. Med. Chem. 15 1011 (1972)).

It is known that several tylosin derivatives have been prepared by the hydrolysis of neutral (J. Am. Chem. Soc. 97 4001 (1975)) and the hydrolysis of basic sugars (J. Am. Chem. Soc. 98 7874 (1976)).

It is also known that 10,11,12,13-tetrahydro derivatives of 19-deformyl-4'-demicarosyl tylosin have been obtained by the catalytical hydrogenation in the presence of palladium-on-charcoal (U.S. Pat. No. 4,345,069 (1982)) and the 10,11,12,13-tetrahydro-5-0-mycaminosyl tylonolide diethyl acetal in the presence of platinum black as catalyst (EP publication 070 170 A1 (1982)).

There are also known hydrogenations in the series of related 16-membered macrolides; e.g. one of the leucomycin A3 derivatives was converted into the tetrahydro derivative in the presence of $PtO_2$ as catalyst, whereby the diene was reduced and the aldehyde was not (Chem. Pharm. Bull. 24 (8) 1749 (1976)).

In chalcomycin, however, wherein a keto group is present as well, it was shown that $PtO_2$ was not selective as there occurred a reduction of the double bond, the epoxy group and the ketone, whereas in the presence of palladium-on-charcoal there were hydrogenated the double bond and the epoxy group (J. Med. Chem. 15 (10) 1011 (1972)).

It has been known as well that a specifically prepared catalyst obtained by the reaction of palladium chloride and sodium borohydride may in several polyfunctional unsaturated compounds hydrogenate the double bond in the presence of carbonyl (J. Org. Chem. 39 3050 (1974)).

Therefore the first object of the present invention are novel tylosin oximes, 10,11,12,13-tetrahydro tylosin, derivatives of 10,11,12,13-tetrahydro tylosin and oximes thereof of the following general formula

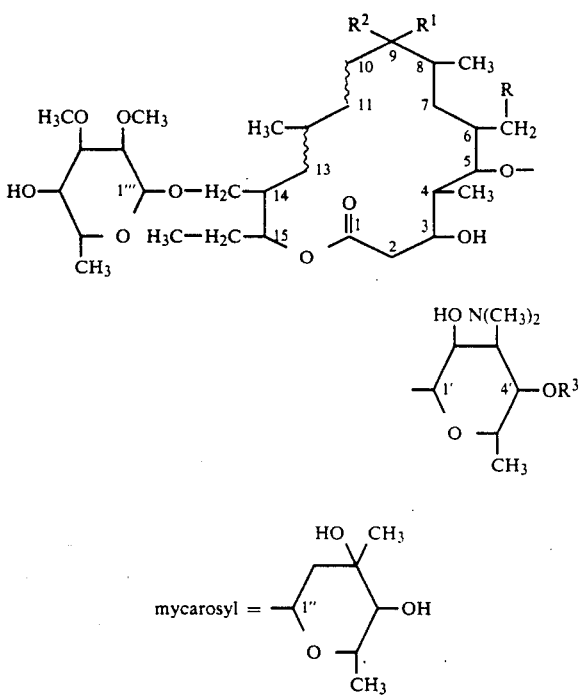

wherein
R stands for CHO, $CH_2OH$, CH=NOH or $CH(OCH_3)_2$,
$R^1$ stands for H,
$R^2$ stands for OH or
$R^1 + R^2$ stands for =O or =NOH,
$R^3$ stands for a mycarosyl group or a hydrogen atom, and
∿ stands for a single or a double bond.

A further object of the present invention are methods for the manufacture of the compounds of the above general formula.

The starting compounds, the intermediates and the produces of the present inventive methods are encompassed by the above general formula and are characterized as follows:

| compound | | | | |
|---|---|---|---|---|
| I | R = CHO, | $R^1,R^2$ = O, | $R^3$ = mycarosyl, | ∿ = double bond |
| Ia | R = $CH_2OH$, | $R^1,R^2$ = O, | $R^3$ = mycarosyl, | ∿ = double bond |
| Ib | R = CHO, | $R^1,R^2$ = O, | $R^3$ = H, | ∿ = double bond |
| Ic | R = $CH(OCH_3)_2$, | $R^1,R^2$ = O, | $R^3$ = mycarosyl, | ∿ = double bond |
| Id | R = $CH(OCH_3)_2$, | $R^1,R^2$ = O, | $R^3$ = H, | ∿ = double bond |
| Ie | R = CHO, | $R^1$ = H, $R^2$ = OH, | $R^3$ = mycarosyl, | ∿ = double bond |
| II | R = CHO, | $R^1,R^2$ = O, | $R^3$ = mycarosyl, | ∿ = single bond |
| III | R = $CH_2OH$, | $R^1,R^2$ = O, | $R^3$ = mycarosyl, | ∿ = single bond |
| IV | R = $CH)OCH_3)_2$, | $R^1,R^2$ = O, | $R^3$ = mycarosyl, | ∿ = single bond |
| V | R = $CH(OCH_3)_2$, | $R^1$ = H, $R^2$ = OH, | $R^3$ = mycarosyl, | ∿ = single bond |
| VI | R = CHO, | $R^1$ = H, $R^2$ = OH, | $R^3$ = mycarosyl, | ∿ = single bond |
| VII | R = CHO, | $R^1,R^2$ = O, | $R^3$ = H, | ∿ = single bond |
| VIII | R = $CH_2OH$, | $R^1,R^2$ = O, | $R^3$ = H, | ∿ = single bond |
| IX | R = $CH(OCH_3)_2$, | $R^1,R^2$ = O, | $R^3$ = H, | ∿ = single bond |
| X | R = $CH(OCH_3)_2$, | $R^1$ = H, $R^2$ = OH, | $R^3$ = H, | ∿ = single bond |

-continued

| compound | | | | |
|---|---|---|---|---|
| XI | R = CHO, | $R^1$ = H, $R^2$ = OH, | $R^3$ = H, | ∼∼∼ = single bond |
| XII | R = CH = NOH, | $R^1,R^2$ = O, | $R^3$ = mycarosyl, | ∼∼∼ = double bond |
| XIII | R = CH(OCH$_3$)$_2$, | $R^1,R^2$ = NOH, | $R^3$ = mycarosyl, | ∼∼∼ = double bond |
| XIV | R = CHO, | $R^1,R^2$ = NOH, | $R^3$ = mycarosyl, | ∼∼∼ = double bond |
| XV | R = CH(OCH$_3$)$_2$ | $R^1,R^2$ = NOH, | $R^3$ = H, | ∼∼∼ = double bond |
| XVI | R = CHO, | $R^1,R^2$ = NOH, | $R^3$ = H, | ∼∼∼ = double bond |
| XVII | R = CH = NOH, | $R^1,R^2$ = NOH, | $R^3$ = mycarosyl, | ∼∼∼ = double bond |
| XVIII | R = CH$_2$OH, | $R^1,R^2$ = NOH, | $R^3$ = mycarosyl, | ∼∼∼ = double bond |
| XIX | R = CH = NOH, | $R^1,R^2$ = O, | $R^3$ = mycarosyl, | ∼∼∼ = single bond |
| XX | R = CH = NOH, | $R^1,R^2$ = NOH, | $R^3$ = mycarosyl, | ∼∼∼ = single bond |
| XXI | R = CH(OCH$_3$)$_2$, | $R^1,R^2$ = NOH, | $R^3$ = mycarosyl, | ∼∼∼ = single bond |
| XXII | R = CHO, | $R^1,R^2$ = NOH, | $R^3$ = mycarosyl, | ∼∼∼ = single bond |
| XXIII | R = CH$_2$OH, | $R^1,R^2$ = NOH, | $R^3$ = mycarosyl, | ∼∼∼ = single bond |

10,11,12,13-tetrahydro tylosin (compound 11) is obtained, in accordance with the present invention, by means of selective catalytical hydrogenation of the diene compound (I) in C-10,11,12,13 positions in the presence of the keto and aldehyde groups. The hydrogenation is preferably performed in ethanol in the presence of palladium-on-charcoal (5-10 mass/mass %) at a hydrogen pressure of 0.2 to 0.5 MPa, at ambient temperature, within 2 to 6 hours.

In the same manner the catalytical hydrogenation of tylosin derivatives, such as relomycin (compound Ia), 9-deoxo-9-hydroxy tylosin (compound Ie) and 4'-demicarosyl compounds thereof, yields 10,11,12,13-tetrahydro relomycin (compound III), 9-deoxo-9-hydroxy-10,11,12,13-tetrahydro tylosin (compound VI) and their 4'-demicarosyl products (compounds VIII, XI).

The hexahydro derivatives (compounds III and VI) are also obtainable by the selective reduction of the aldehyde or keto group resp., depending on the reaction conditions, with sodium borohydride, starting from 10,11,12,13-tetrahydro tylosin (compound II).

The performing of the reaction in a mixture of methanol and a phosphate buffer of a pH 7.5 results in the reduction of the aldehyde group in C-20 position, whereas the ketone in C-9 position remains unaltered. In anhydrous alcohol there occurs a simultaneous reduction of the keto and aldehyde group. To inhibit the reduction of the aldehyde, the protection of the aldehyde group is performed by acetalization of the 10,11,12,13-tetrahydro tylosin (compound II). The obtained acetal (IV) makes possible only the reduction of the keto group and, accordingly, there is obtained the 9-deoxo-9-hydroxy-10,11,12,13-tetrahydro tylosin dimethyl acetal (compound V); via the hydrolysis of the acetal there is obtained the desired 9-deoxo-9-hydroxy-10,11,12,13-tetrahydro tylosin (compound VI).

The acetalization may be performed with methanol or ethanol in anhydrous conditions in the presence of a catalytical quantity of an organic acid, such as trifluoroacetic acid, and the hydrolysis of the acetal may be performed in acetonitrile (50%) in the presence of a catalytic quantity of an organic or inorganic acid, such as trifluoroacetic or hydrochloric acid.

The reduction is performed at ambient temperature with sodium borohydride (0.7-2.0 mole) within 2 to 10 hours.

The oximes of tylosin and of its derivatives (compounds XII-XXIII) are prepared in accordance with the invention by means of oximation of tylosin and of its hydrogenated derivatives with hydroxylamine or its acid addition salts, and the site and the degree of oximation depend on the reaction conditions.

The reaction may be performed with a 1 to 10 molar excess of hydroxylamine hydrochloride in the presence of an excess of a slightly basic tertiary amine (preferably pyridine) or an inorganic base (e.g. Na$_2$CO$_3$) in the presence of a solvent, such as an alcohol, or in absence of any solvent, using the organic base as the reaction medium, at a temperature of 0° to 100° C. within 15 minutes to 10 hours. The presence of the C-9 keto and C-20 aldehyde groups in the tylosin (I) makes possible the obtaining of mono- and dioxime derivatives.

The selective oximation of the C-20 group in the presence of the C-9 keto group is achieved by the reaction of tylosin (I) with one equivalent of hydroxylamine hydrochloride in alcohol in the presence of a limited quantity of a base (pyridine or Na$_2$CO$_3$), at a temperature of 0° to 100° C., within a few minutes to 10 hours, yielding the desired aldoxime (compound XII).

For the selective oximation of the C-9 keto group the aldehyde group has to be protected, which is achieved by acetalisation and the obtained acetals (compounds XIII, XV, XXI) are subjected to the hydrolysis of the protective group, whereupon there are isolated the desired C-9 oximes: tylosin oxime (XIV), 4'-demicarosyl tylosin oxime (XVI) and 10,11,12,13-tetrahydro tylosin oxime (XXII).

The preparation of the dioximes may be performed in a single step or in two steps. In order to obtain the tylosin dioxime (XVII) the preparation is performed in two steps by the reoximation of the isolated tylosin aldoxime (compound XII). The preparation of the 10,11,12,13-tetrahydro tylosin dioxime is achieved by a single-step process, by means of a 5 molar excess of hydroxylamine hydrochloride in the presence of a 2.5 molar excess of Na$_2$CO$_3$.

The isolation of the product is performed by conventional methods, e.g. by precipitation or extraction with halogenated solvents from aqueous alkaline solutions and the evaporation into a dry residue.

Prior to spectrum analysis the products are purified on a silicagel column.

The 10,11,12,13-tetrahydro derivatives are identified as the disappearance of the diene significantly changes the spectrum characteristics: there disappear the characteristic signals in the range of 134-148 ppm in the $^{13}$C-NMR spectrum and 5.5-7.3 ppm in the $^1$H-NMR spectrum. In the IR spectrum the disappearance of the dienone induces the shift of the carbonyl band towards shorter wave lengths.

For the tylosin oximes in the $^{13}$C-NMR spectra there disappears the characteristic carbonyl signal in the 200 ppm area and there appears a new chemical shift in the range of 150-165 ppm, characteristic for C=N.

In the ¹H-NMR spectrum of the obtained aldoximes there disappears the characteristic shift for the aldehydes in the area of 9.6 ppm and new ones appear in the range of 10.0.-10.7 ppm, corresponding to the =NOH group, which disappear after the agitation with $D_2O$.

The present invention yields hitherto not described 10,11, 12,13-tetrahydro derivatives of tylosin compounds II-XI), tylosin oximes and 10,11,12,13-tetrahydro tylosin oximes (XII-XXIII) and several of them exhibit a significant biological activity.

The antimicrobial activity of some compounds of the present invention was tested on the laboratory strain Sarcina lutea and on 50 various strains isolated from fresh patients' samples. The minimal inhibitory concentration (MIC) was determined by the agar dilution method as described by M. D. Finegold and J. W. Martin, Diagnostic Microbiology, Mosby Comp., St. Louis 1982, p. 536-540.

Some test results are represented in the following Table.

Therefore a further object of the present invention is a pharmaceutical composition comprising an effective amount of the new compounds of the present invention, a method of treating microbial human and animal infections, and a method for the manufacture of pharmaceuticals comprising the novel compounds of the present invention.

(C-20), 171.95 (C-1) 103.58 (C-1'), 100.89 (C-3'''), 95.98 C-1'')
UV (EtOH) ν max. 203 nm, logε 3.39
IR (CHCl₃) 1725, 1710 cm⁻¹
Mass spectrum m/e 919 (M+)

Method B

In 200 ml of ethanol there were dissolved 10 g of tylosin (I), whereupon there were added 0.50 g of palladium-on-charcoal (5%) and it was hydrogenated at a hydrogen pressure of 0.2 MPa for 6 hours at ambient temperature. The isolation was performed as described in method A) or by a partial evaporation of ethanol and a subsequent precipitation with ether or n-hexane. Yield: 8.0 g (79.6%). The obtained product was identical with the product of Example 1A.

EXAMPLE 2

10,11,12,13-tetrahydro relomycin (III)

Method A

In 180 ml of ethanol there were dissolved 4 g of relomycin (Ia), whereupon there were added 0.8 g of palladium-on-charcoal (10%) and it was hydrogenated for 3 hours at a hydrogen pressure of 0.5 MPa at ambient temperature. The isolation was performed as described in Example 1A.

TABLE I

| Strain | No. of test strains | Minimal Inhibitory Concentration (mcg/ml)ᵃ | | | | | | | |
|---|---|---|---|---|---|---|---|---|---|
| | | Ia | II | III | VI | XII | XVIII | XIX | XX | XXIII |
| Strep. pneumoniae | 3 | 0.5-1.0 | 0.5 | R | 0.5 | 0.5 | 0.5 | 1.0 | 2.0-4.0 | 64.0 |
| Strep. faecalis | 17 | 64.0 | 4.0-8.0 | R | 8.0-32.0 | 1.0-4.0 | R | — | — | R |
| Strep. agalact. | 2 | 16.0 | 1.0-2.0 | R | 2.0-8.0 | 0.5 | 64.0 | — | — | R |
| Staph. aureus | 13 | 4.0-16.0 | 2.0-4.0 | 32.0 | 4.0 | 1.0-4.0 | 64.0 | 8.0-16.0 | 16.0-32.0 | R |
| Staph. saproph. | 6 | 1.0-16.0 | 1.0-2.0 | R | 2.0-4.0 | 0.5-2.0 | 4.0-16.0 | 8.0 | 16.0 | R |
| Sarcina lutea | 4 | 1.0 | 0.5 | 1.0 | 0.5 | 0.5 | 0.5 | 0.5 | 1.0 | 0.5 |

Ia = relomycin
II = 10,11,12,13-tetrahydro tylosin
III = 10,11,12,13-tetrahydro relomycin
VI = 9-deoxo-9-hydroxy-10,11,12,13-tetrahydro tylosin
XII = tylosin aldoxime
XVIII = relomycin oxime
XIX = 10,11,12,13-tetrahydro tylosin aldoxime
XX = 10,11,12,13-tetrahydro tylosin dioxime
XXIII = 10,11,12,13-tetrahydro relomycin oxime
R = resistant
a = the obtained MIC values refer to over 90% of tested strains The invention is illustrated but in no way limited by the following Examples.

EXAMPLE 1

10,11,12,13-tetrahydro tylosin II)

Method A

In 200 ml of ethanol there were dissolved 10 g of tylosin (I), whereupon there were added 0.25 g of palladium-on-charcoal 10%) and it was hydrogenated for 6 hours at ambient temperature and at a hydrogen pressure of 0.2 MPa. The completion of the reaction was determined chromatographically (Silicagel F₂₅₄; methylene chloride-methanol-ammonium hydroxide 90:9:1.5) (System A). The catalyst was separated by filtration the ethanol was evaporated at reduced pressure and the product was dried to a constant mass. Yield 9.4 g (93.5%). The product purified by column chromatography had the following characteristics:

¹H-NMR (CDCl₃) δ ppm 9.96 (H, s, C-20), 3.61 (3H, s, 3'''OCH₃), 3.50 (3H, s, 2'''OCH₃), 2.49 (6H, s, N(CH₃)₂) ¹³C-NMR(CDCl₃) δ ppm 214.51 C-9), 202.77

Yield: 3.7 g (92%). After purification by column chromatography the product exhibited the following characteristics:

¹H-NMR (CDCl₃) δ ppm 3.61 (3H, s, 3'''0CH₃), 3.51 (3H, s, 2'''OCH₃). 2.49 (6H, s, N(CH₃)₂)
¹³C-NMR (CDCl₃) δ ppm 214.69 (C-9), 171.72 (C-1), 103.58 (C-1'), 100.88 (C-1'''), 95.98 (C-1'')
UV (EtOH) λ$_{max}$.283 nm, log ε 1.99
IR (CHCl₃) 1725, 1710 cm.⁻¹
Mass spectrum (m/e) 921 (M+)

Method B 10,11,12,13-tetrahydro tylosin (II) (5 g, 5.4 mmole) was dissolved in 75 ml of methanol, whereupon there were added 15 ml of a 0.4M phosphate buffer (pH 7.5) and 0.15 g (4.0 mmole) of sodium borohydride. The reaction mixture was stirred for 2 hours at ambient temperature, the methanol was evaporated at reduced pressure, there were added 75 ml of water and it was extracted with chloroform(three 25 ml portions). The combined extracts were washed with a saturated solution of sodium chloride and dried over $K_2CO_3$. The evaporation of the solvent yielded 4.1 g (82%) of a dry residue; this product was identical with the product obtained according to the process of Example 2A.

EXAMPLE 3

10,11,12,13-tetrahydro tylosin dimethyl acetal (IV)

10,11,12,13-tetrahydro tylosin (II) (5 g, 5.4 mmole) was dissolved in 100 ml of dry methanol and there was added 1 ml of trifluoroacetic acid. After standing for 2 days at ambient temperature there was added a saturated solution of sodium hydrocarbonate in order to adjust the pH of the solution to 8–8.5, whereupon the methanol was evaporated, there were added 30 ml of water and was extracted with chloroform (three 10 ml portions). The combined extracts were washed with a saturated solution of sodium chloride and dried with $K_2CO_3$, whereupon it was evaporated to obtain a dry residue.

Yield: 4.75 g of the crude product. By purification on a silicagel column (chloroform-methanol-ammonium hydroxide 6:1:0.1) (System B) there were obtained 2.85 g of 10,11,12,13-tetrahydro tylosin dimethyl acetal (IV).

$^1$H-NMR (CDCl$_3$) δ ppm 3.61 (3H, s, 3'''OCH$_3$), 3.49 (3H, s, 2'''OCH$_3$), 3.28 (3H, s, 20-OCH$_3$), 3.23 (3H, s, 20-OCH$_3$), 2.49 (6H, s, N(CH$_3$)$_2$)

$^{13}$C-NMR (CDCl$_3$) δ ppm 214.51 (C-9), 171.95 (C-1), 103.58 (C-1), 102.18 (C-20), 100.89 (C-1'''), 96.22 (C-1''), 61.66 (C-3'''OCH$_3$), 59.61 (C-2'''OCH$_3$), 53.19 (C-20 OCH$_{20}$), 49.75 (C-20 OCH$_3$)

EXAMPLE 4

9-deoxo-9-hydroxy-10, 11,12,13-tetrahydro tylosin dimethyl acetal (V)

10,11,12,13-tetrahydro tylosin dimethyl acetal (IV) (2 g, 2.2 mmole) was dissolved in 40 ml of dry ethanol, there were added 0.15 g (4 mmole) of sodiumborohydride and it was stirred for 10 hours at ambient temperature. After the evaporation of ethanol at reduced pressure and the addition of 40 ml of water it was extracted with chloroform. The extracts were washed with a saturated solution of sodium chloride, dried over $K_2CO_3$ and evaporated to obtain a dry residue.

Yield: 1.6 g (79.8%)

$^1$H-NMR (CDCl$_3$) δ ppm 3.61 (3H, s, 3'''OCH ), 3.51 (3H, s, 2'''OCH$_3$), 3.28 (3H, s, 20-OCH$_3$), 3.23 (3H, s, 20-OCH$_3$), 2.49 (6H, s, N(CH$_3$)$_2$)

$^{13}$C-NMR (CDCl$_3$) δ ppm 171.95 (C-1), 103.58 (C-1'), 102.18 (C-20), 100.89 (C-1'''), 96.22 (C-1''), 61.66 (C-3'''OCH$_3$), 59.61 (C-2'''OCH$_3$), 53.19 (C-20 OCH$_3$), 49.75 (C-20 OCH$_3$)

EXAMPLE 5

9-deoxo-9-hydroxy-10,11,12,13-tetrahydro tylosin (VI)

Method A 9-deoxo-9-hydroxy-10,11,12,13-tetrahydro tylosin dimethyl acetal (V) (2 g, 2 mmole) was dissolved in 50 ml of acetonitrile, whereupon there were added 50 ml of water and 0.2 ml of trifluoroacetic acid. After stirring for two hours at ambient temperature the reaction solution was alkalized to a pH value of 8–8.5 by the addition of a saturated solution of sodium hydrogen carbonate and it was extracted with chloroform. The combined extracts were washed with a saturated sodium chloride solution and dried over $K_2CO_3$.

The crude product (1.5 g) was purified on a silicagel column.

Yield: 1.1 g (57.9%) of a product with the following characteristics:

$^1$H-NMR (CDCl$_3$) δ ppm 9.67 (H, S, C-20, 3.61 (3H, s, 3'''OCH$_3$), 3.51 (3H, s, 2'''OCH$_3$), 2.49 (6H, s, N(CH$_3$)$_2$) $^{13}$C-NMR (CDCl$_3$) δ ppm 202.73 (C-20), 171.95 C-1), 103.58 (C-1'), 100.89 (C-1'''), 96.22 (C-1'')

Method B

In 50 ml of ethanol there was dissolved 1 g of 9-deoxo-9-hydroxy-tylosin (Ie), whereupon there were added 0.35 g of palladium-on-charcoal (10% ) and it was hydrogenated for 3 hours at ambient temperature and a hydrogen pressure of 0.5 MPa. The isolation as described in Example 1A yielded 0.9 g (89.6%) of the hydrogenated product of equal characteristics as the product obtained according to the method 5A.

EXAMPLE 6

4'-demicarosyl-10,11,12,13-tetrahydro tylosin (VII)

In 50 ml of ethanol there was dissolved 1 g of 4'-demicarosyl tylosin (Ib) and it was hydrogenated as described in Example 4. The isolation performed as described in Example 1A yielded 0.91 g of the product.

$^{13}$C-NMR (CDCl$_3$) δ ppm 214.51 (C-9), 202.77 (C-20), 171.95 (C-1), 103.57 (C-1'), 100.89 (C-1''')

$^1$H-NMR (CDCl$_3$) δ ppm 3.61 (3H, s, 340 ''OCH$_3$), 3.51 (3H, s, 7 2'''OCH$_3$), 2.49 (6H, s, N(CH$_3$)$_2$)

EXAMPLE 7

4'-demicarosyl-10,11,12,13-tetrahydro relomycin (VIII)

Method A

In 50 ml of ethanol there was dissolved 1 g of 4'-demicarosyl relomycin, there were added 0.3 g of palladium-on-charcoal (10%) and it was hydrogenated for 2 hours at ambient temperature and a hydrogen pressure of 0.5 MPa. The isolation according to Example 1A yielded 0.9 g of the product.

$^1$H-NMR (CDCl$_3$) δ ppm 3.61 (3H, 3'''OCH$_3$), 3.51 (3H, s, 2'''OCH$_3$), 2.49 (6H, s, N(CH$_3$)$_2$)

$^{13}$C-NMR (CDCl$_3$) δ ppm 214.70 (C-9), 171.72 (C-1), 103.58 (C-1'), 100.89 (C-1''')

Method B

4'-demicarosyl-10,11,12,13-tetrahydro tylosin (VII) (5 g, 6.4 mmole) was dissolved in 70 ml of methanol, whereupon there were added 14 ml of a 0.4M phosphate buffer (pH 7.5) and 0.24 g (6.4 mmole) of sodium borohydride. The reaction mixture was stirred for 2 hours at ambient temperature, the methanol was evaporated at reduced pressure; there were added 75 ml of water and it was extracted with chloroform (three 25 ml portions). The combined extracts were washed with a saturated solution of sodium chloride and dried over $K_2CO_3$. The evaporation of the solvent yielded, as a dry residue, 4.2 g (84.5%) of the product, identical to the product of method 7A.

EXAMPLE 8

4'-demicarosyl-9-deoxo-9-hydroxy-10,11,12,13-tetrahydro tylosin (XI)

4'-demicarosyl-10,11,12,13-tetrahydro tylosin (VII) (2.3 g, 3.0 mmole) was dissolved in 50 ml of dry methanol. Then there were added 3.07 ml of trifluoroacetic acid. After 2 days there was isolated the 4'-demicarosyl- 10,11,12,13-tetrahydro tylosin dimethyl acetal (IX) as described in Example 3. The crude product (2 g, 2.43 mmole) was dissolved in 30 ml of dry ethanol. To the solution there were added 0.14 g (3.7 mmole) of sodium borohydride and it was stirred for 6 hours at ambient temperature. The ethanol was evaporated at reduced pressure, whereupon there were added 30 ml of water and it was extracted with chloroform. The combined extracts were dried and evaporated to obtain a dry residue. 1.8 g of the obtained 4'-demicarosyl-9-deoxo-9-hydroxy-10,11,12,13- tetrahydro tylosin dimethyl acetal(X) were subjected to the hydrolysis of the acetal as described in Example 5A.

Yield: 1.5 g (79.4%) of the title product of the following characteristics:

$^1$H-NMR (CDCl$_3$) δ ppm 9.67 (H, s, C-20 , 3.60 (3H, s, 3'''OCH$_3$), 3.50 (3H, s, 2'''OCH), 2.49 (6H, s, N(CH$_3$)$_2$)

$^{13}$C-NMR (CDCl$_3$) δ ppm 202.73 C-20), 171.99 (C-1), 103.56 (C-1'), 100.87 (C-1''')

EXAMPLE 9

Tylosin aldoxime (XII)

Tylosin (I) (4.58 g, 5.0 mmole) was dissolved in ethanol (100 ml) and, under stirring, there were added pyridine (2.5 ml) and hydroxylamine hydrochloride (0.348 g, 5 mmole) and it was kept at the boil under a reflux cooler for 15 minutes in a nitrogen stream. After cooling 50 ml of water were added to the reaction mixture and the pH value was adjusted to 7.0 with 1 H NaOH. Then it was concentrated under reduced pressure to ⅓ of the volume and extracted with chloroform (2×150 ml). The chloroform extracts were combined and dried over K$_2$CO$_3$), filtered and evaporated to dryness, yielding 3.95 g (84.9%) of the product in the form of a mixture of isomers, which were separable on a silicagel column (System A).

IR (CHCl$_3$) 1585, 1670, 1705, disappearance of the band at 2720 cm$^{-1}$

UV (EtOH) λ $_{max}$ 283 nm, logε 4.3

$^1$H-NMR (DMSO-d$_6$) δ ppm 10.07 (=N—OH, C-20, disappeared after agitation with D$_2$O, 7.19 (H, d, H-11), 6.46 (H, d, H-10), 5.87 (H, d, H-13)

$^{13}$C-NMR (DMSO-d$_6$) δ ppm 202.72 (C-9), 172.46 (C-1), 149.83 (C-20), 147.12 (C-11), 142.14 (C-13), 134.86 (C-12), 118.90 (C-10), 103.89 (C-1'), 100.73 (C-1'''), 96.05 (C-1'')

M+930

EXAMPLE 10

Tylosin oxime dimethyl acetal (XIII)

Tylosin dimethyl acetal (Ic) (4.40 g, 4.6 mmole) was dissolved in 20 ml of pyridine, there was added hydroxylamine hydrochloride (2.76 g, 39.7 mmole) and it was stirred in a nitrogen stream at ambient temperature for 9 hours. To the reaction mixture 200 ml of water were added and it was alkalized with 1N NaCH to a pH value of 9.0, whereupon it was concentrated under reduced pressure and extracted with chloroform ( 1×200 ml). The chloroform layer was dried over K$_2$CO$_3$ and filtered. The filtrate was evaporated to dryness, yielding 3.9 g (86.9%) of the crude product. 2.0 g of the product were purified by chromatography on 200 g of silicagel (System A).

There were obtained 1.50 g of the pure title product of the following physical-chemical constants:

R$_f$(A) 0.443

R$_f$(B) 0.786

IR (KBr) 1710, 1610 cm$^{-1}$

UV (EtOH) λ $_{max}$ 272 nm, logε 4.18

$^1$H NMR (DMSO-d$_6$) δ ppm 10.51 (=N—OH), disappeared after agitation with D$_2$O, 7.07 (1H, d, H-11), 6.17 (1H, d, H-10), 5.56 (1H, d, H-13), 3.46 (3H, s, 3'''OCH$_3$), 3.37 (3H, s, 2'''OCH$_3$), 3.20 (6H, s, 2×20-(OCH$_3$)), 2.41 (6H, s, N(CH$_3$)$_2$) M+ 976

EXAMPLE 11

Tylosin oxime (XIV)

Tylosin oxime dimethyl acetal (XIII) (1.9 g, 1.95 mmole) was dissolved in 50 ml of acetonitrile, whereupon there were added 50 ml of water and 0.2 ml of trifluoroacetic acid. After stirring for 3 hours at ambient temperature, there were isolated, according to the method of Example 5, 1.15 g of the crude product, which was purified on a silicagel column.

Yield: 0.65 (35.8%) of the product with the following characteristics:

R$_f$(A) 0.314

$^1$H-NMR (DMSO-d$_6$) δ ppm 10.65 (=N—OH), disappeared after agitation with D$_2$O, 9.65 (1H, s,—CHO)

EXAMPLE 12

4'-demicarosyl tylosin oxime dimethyl acetal (XV)

2.0 g (2.45 mmole) of 4'-demicarosyl tylosin dimethyl acetal (Id), 20 ml of pyridine and 1.38 g (19.86 mmole) of hydroxylamine hydrochloride were stirred in a nitrogen stream at ambient temperature for 4 hours, whereupon it was isolated in accordance with the method of Example 10.

Yield: 1.7 g (83.4%) of the product with the following characteristics:

R$_f$(A) 0.253,

R$_f$(D) 0.599

UV (EtOH) λ$_{max}$ 272 nm, logε 4.26

IR (KBr) 1705, 1615 cm$^{-1}$ $^1$H-NMR (DMSO-d$_6$) δ ppm 10.65 (=N—OH), disappeared after agitation with D$_2$O, 3.20 (6H, s, 20-(OCH$_3$)$_2$)

EXAMPLE 13

4'-demicarosyl tylosin oxime (XVI)

The title product (XV) of Example 12 (1.43 g, 1.72 mmole) was dissolved in 40 ml of a mixture of 0.1N HCl and CH$_3$CN (2.5:1) and stirred for 2 hours at ambient temperature, whereupon it was isolated as described in Example 5.

The crude product (1.25 g) was purified on a silicagel column.

Yield: 0.95 g (70.3%) of the product with the following characteristics:

R$_f$(A) 0.146,

R$_f$(B) 0.468

UV (EtOH) λ$_{max}$ 272 nm, logε 4.26

$^1$H-NMR (DMSO-d$_6$) δ ppm 10.65 (=N-OH), disappeared after agitation with D$_2$O, 9.65 (H, s,—CHO)

EXAMPLE 14

Tylosin dioxime (XVII)

The crude title product (XII) of Example 9 (2.93 g, 3.15 mmole) was dissolved in 20 ml of methanol, whereupon there were added 1.6 ml of pyridine and 0.22 g (3.16 mmole) of hydroxylamine hydrochloride and it was refluxed in a nitrogen stream for 10 hours. After cooling 40 ml of water were added to the reaction mixture and it was alkalized with 1N NaOH to a pH value of 9.0 and, subsequently, concentrated to ⅓ of the volume. The suspension was stirred for 1 hour and filtered. The obtained precipitate was resuspended in 10 ml of water, stirred for 10 minutes, filtered and washed with water yielding 1.4 g of the product.

The initial filtrate and the filtered washings were combined and extracted with chloroform. The combined extracts were washed with water and dried over $K_2CO_3$, yielding 0.7 g of the product.

Total yield: 2.1 g (70.6%) of the product of the following characteristics:

IR (KBr) 1705, 1630 $cm^{-1}$
UV (EtOH) $\lambda_{max}$ 272 nm, $\log \epsilon$ 4.2
$^1$H-NMR (DMSO-$d_6$) δ ppm 10.66 and 10.11 (2×=N—OH) disappeared after agitation with $D_2O$

EXAMPLE 15

Relomycin oximine (XVIII)

Relomycin (Ia) (15 g, 16.6 mmole) was dissolved in 75 ml of pyridine, whereupon there was added hydroxylamine hydrochloride (5.64 g, 81.2 mmole) and it was stirred in a nitrogen stream for 7 hours at ambient temperature. The crude title product (13.8 g) was isolated in accordance with the method described in Example 14.

The crude product (2.9 g) was purified on a silicagel column. There were obtained 1.2 g of the pure product of the following characteristics:

$R_f$(A) 0.302,
$R_f$(C) ($CH_2Cl_2$: $CH_3OH$=85:15) 0.462
UV (EtOH) $\lambda_{max}$ 272 nm, $\log \epsilon$ 4.21
IR (KBr) 1700, 1630 $cm^{-1}$
$^1$H-NMR (DMSO-$d_6$) δ ppm 10.66 (=N—OH), disappeared after agitation with $D_2O$
$^{13}$C-NMR (CDCl$_3$) δ ppm 173.99 (C-1), 160.45 (C-9, C=N), 137.03 (C-11), 135.58 (C-13), 134.78 (C-12), 117.07 (C-10), 105.21 (C-1'), 100.83 (c-1'''), 95.99 (C-1'')
788 ($M^+$ - mycarose)

EXAMPLE 16

10,11,12,13-tetrahydro tylosin aldoxime (XIX) and 10,11,12,13tetrahydro tylosin dioxime (XX)

10,11,12,13-tetrahydro tylosin (II) (3.68 g, 4.0 mmole) was dissolved in 20 ml of methanol, whereupon there were added hydroxylamine hydrochloride (1.39 g, 20.0 mmole) and $Na_2CO_3$ (1.06 g, 10.0 mmole) and it was refluxed for 3 hours. 40 ml of water were added to the cooled reaction mixture, the pH value was adjusted to 7.0 with 1N NaOH and it was extracted with chloroform. The crude product (3.2 g) was a mixture of two compounds, separable on a silicagel column (system A).

Yield: 0.95 g (25.4%) of a more polar product (XIX) of the following characteristics:

$R_f$(B) 0.429
$^1$H-NMR (DMSO-$d_6$) δ ppm 10.17 (=N—OH, C-20), disappeared after agitation with $D_2O$
$^{13}$C-NMR (DMSO-$d_6$) δ ppm 213.40 (C-9), 171.22 (C-1), 150.9 (C-20), 104.91 (C-1'), 100.57 (C-1''') 96.17 (C-1'')
$M^+$ 934

Yield: 0.90 g (23.7%) of a less polar product (XX) with the following characteristics:

$R_f$(B) 0.366
$^1$H-NMR (DMSO-$d_6$) δ ppm 10.62 and 10.17 (2×=N—OH), disappeared after agitation with $D_2O$ $^{13}$C-NMR (DMSO-$d_6$) δ ppm 171.17 (C-1), 150.79 (C-20), 150.18 (C-9), 104.74 (C-1'), 100.51 (C-1'''), 96.11 (C-1'')
$M^+$ 949

EXAMPLE 17

10,11,12,13-tetrahydro tylosin oxime dimethyl acetal (XXI)

From 4.25 g (4.4 mmole) of 10,11,12,13-tetrahydro tylosin dimethyl acetal (IV), dissolved in 20 ml of pyridine and 2.76 g (39.7 mmole) of hydroxylamine hydrochloride, there were obtained 3.5 g of the crude product, in accordance with the method of Example 10.

1.5 g of the crude product were purified on a silicagel column (System A), yielding 1.0 g of the pure title product of the following characteristics:

IR (KBr) 1700, 1620 $cm^{-1}$
$^1$H-NMR (DMSO-$d_6$) δ ppm 10.65 (=N—OH, C-9), disappeared after agitation with $D_2O$, 3.23 (6H, s, 20-($OCH_3$)$_2$)
$^{13}$C-NMR (DMSO-$d_6$) δ ppm 171.17 (C-1), 150.23 (C-9)

EXAMPLE 18

10,11,12,13-tetrahydro tylosin oxime (XXII)

From the crude product (XXI) of Example 17 (2.0 g, 2.1 mmole), 50 ml of acetonitrile, 50 ml of water and 0.2 ml of trifluoroacetic acid there were isolated - in accordance with the process of Example 5A - 1.6 g of the crude title product. After purification on a silicagel column there were obtained 1.2 g (61.2%) of the product with the following characteristics:

$^1$H-NMR (DMSO-$d_6$) δ ppm 10.65 (=N—OH, C-9), disappeared after agitation with $D_2O$, 9.65 (H, s, —CHO)
$^{13}$C-NMR DMSO-$d_6$) δ ppm 202.72 (C-20), 171.17 (C-1), 150.18 (C-9)

EXAMPLE 19

10,11,12,13-tetrahydro relomycin oxime (XXIII)

From 3.68 g (4 mmole) of 10,11,12,13-tetrahydro relomycin (III), 20 ml of pyridine and 1.38 g (19.86 mmole) of hydroxylamine hydrochloride there were obtained—in accordance with the process of Example 10 - 2.86 g (76.4%) of the crude product.

The crude product (1.5 g) was purified on a silicagel column (CHCl$_3$:C$_2$H$_5$OH NH$_4$OAc 15% 85:15:1 (System D), yielding 1.06 g of the pure title product of the following characteristics:

IR (KBr) 1700, 1640 $cm^{-1}$
$^1$H-NMR (DMSO-$d_6$) δ ppm 9.95 (=N—OH), disappeared after agitation with $D_2O$
$^{13}$C-NMR (CDCl$_3$) δ ppm 172.30 (C-1), 165.06 (C-9, C=N)
$M^+$ 936

What is claimed is:
1. A compound of formula I

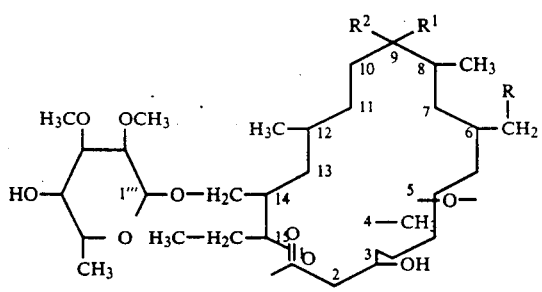

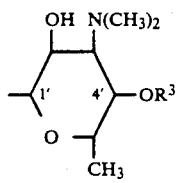

wherein
R stands for CHO, CH$_2$OH or CH(OCH$_3$)$_2$;
R$^1$ represents H;
R$^2$ represents OH; or
R$^1$ and R$^2$ are together O;
R$^3$ represents mycarosyl or H;
under the provision that R is not CHO when R$^1$ and R$^2$ stand together for O.

2. A compound of formula I of claim 1, wherein R represents CH$_2$OH, R$^1$ and R$^2$ are together O, and R$^3$ is mycarosyl.

3. A compound of formula I of claim 1, wherein R represents CH(OCH$_3$)$_2$, R$^1$ and R$^2$ are together O, and R$^3$ is mycarosyl.

4. A compound of formula I of claim 1, wherein R represents CH(OCH$_3$)$_2$, R$^1$ is H, R$^2$ is OH, and R$^3$ is mycarosyl.

5. A compound of formula I of claim 1, wherein R represents CHO, R$^1$ is H, R$^2$ is OH, and R$^3$ is mycarosyl.

6. A compound of formula I of claim 1, wherein R represents CH$_2$OH, R$^1$ and R$^2$ are together O, and R$^3$ is H.

7. A compound of formula I of claim 1, wherein R represents CH(OCH$_3$)$_2$, R$^1$ and R$^2$ are together O, and R$^3$ is H.

8. A compound of formula I of claim 1, wherein R represents CH(OCH$_3$)$_2$, each of R$^1$ and R$^3$ is H, and R$^2$ is OH.

9. A compound of formula I of claim 1, wherein R represents CHO, each of R$^1$ and R$^3$ is H, and R$^2$ is OH.

10. A compound of formula Ia

R stand for CHO, CH(OCH$_3$)$_2$, CH$_2$OH or CH=NOH;
R$^1$ represents O or NOH;
R$^2$ represents mycarosyl or H;
~~~ is a single or a double bond;
under the provision that R or R$^1$ stand for CH=NOH or NOH.

11. A compound of formula Ia of claim 10, wherein R stands for CH=NOH, R$^1$ represents O, R$^2$ represents mycarosyl, and ~~~ is a double bond.

12. A compound of formula Ia of claim 10, wherein R stands for CH(OCH$_3$)$_2$, R$^1$ represents NOH, R$^2$ represents mycarosyl, and ~~~ is a double bond.

13. A compound of formula Ia of claim 10, wherein R stands for CHO, R$^1$ represents NOH, R$^2$ represents mycarosyl, and ~~~ is a double bond.

14. A compound of formula Ia of claim 10, wherein R stands for CH(OCH$_3$)$_2$, R$^1$ represents NOH, R$^2$ represents H, and ~~~ is a double bond.

15. A compound of formula Ia of claim 10, wherein R stands for CHO, R$^1$ represents NOH, R$^2$ represents H, and ~~~ is a double bond.

16. A compound of formula Ia of claim 10, wherein R stands for CH=NOH, R$^1$ represents NOH, R$^2$ represents mycarosyl, and ~~~ is a double bond.

17. A compound of formula Ia of claim 10, wherein R stands for CH$_2$OH, R$^1$ represents NOH, R$^2$ represents mycarosyl, and ~~~ is a double bond.

18. A compound of formula Ia of claim 10, wherein R stands for CH=NOH, R$^1$ represents O, R$^2$ represents mycarosyl, and ~~~ is a single bond.

19. A compound of formula Ia of claim 10, wherein R stands for CH=NOH, R$^1$ represents NOH, R$^2$ represents mycarosyl, and ~~~ is a single bond.

20. A compound of formula Ia of claim 10, wherein R stands for CH(OCH$_3$)$_2$, R$^1$ represents NOH, R$^2$ represents mycarosyl, and ~~~ is a single bond.

21. A compound of formula Ia of claim 10, wherein R stands for CHO, R$^1$ represents NOH, R$^2$ represents mycarosyl, and ~~~ is a single bond.

22. A compound of formula Ia of claim 10, wherein R stands for CH$_2$OH, R$^1$ represents NOH, R$^2$ represents mycarosyl, and ~~~ is a single bond.

23. A method of treating microbial infections in humans or animals, which comprises administering an antimicrobial composition containing a pharmaceutically effective amount of a compound of claim 1.

24. A method of treating microbial infections in human or animal which comprises administering an antimicrobial composition containing a u pharmaceutically effective amount of a compound of claim 10.

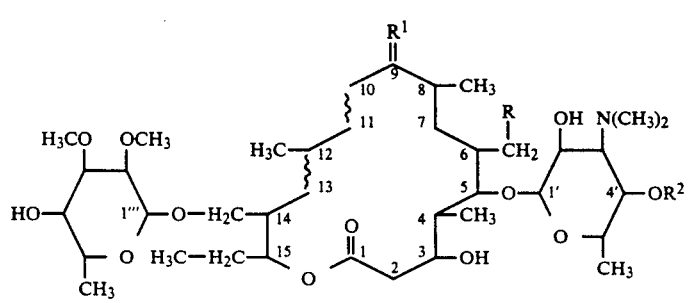

wherein

* * * * *